United States Patent [19]

Stevens

[11] Patent Number: 5,722,981
[45] Date of Patent: Mar. 3, 1998

[54] DOUBLE NEEDLE LIGATURE DEVICE

[75] Inventor: Jon A. Stevens, Condado, Puerto Rico

[73] Assignee: Tahoe Surgical Instruments, San Juan, Puerto Rico

[21] Appl. No.: 731,689

[22] Filed: Oct. 17, 1996

Related U.S. Application Data

[63] Continuation of Ser. No. 255,363, Jun. 8, 1994, abandoned, which is a continuation-in-part of Ser. No. 134,263, Oct. 8, 1993, Pat. No. 5,462,560.

[51] Int. Cl.⁶ ............................................. A61B 17/04
[52] U.S. Cl. ........................... 606/148; 606/144; 606/222
[58] Field of Search ........................... 606/139, 222, 606/224, 144–148; 112/80.03, 169; 604/15, 158, 161, 164, 165, 170

[56] References Cited

U.S. PATENT DOCUMENTS

| | | | |
|---|---|---|---|
| 2,670,673 | 3/1954 | Gordon et al. | 99/257 |
| 4,316,469 | 2/1982 | Kapitanov | 128/334 R |
| 4,665,906 | 5/1987 | Jervis | 128/92 YN |
| 4,779,616 | 10/1988 | Johnson | 128/334 R |
| 5,037,433 | 8/1991 | Wilk et al. | 606/139 |
| 5,067,957 | 11/1991 | Jervis | 606/108 |
| 5,190,546 | 3/1993 | Jervis | 606/78 |
| 5,219,358 | 6/1993 | Bendel et al. | 606/222 |
| 5,242,427 | 9/1993 | Bilweis | 604/264 |
| 5,250,054 | 10/1993 | Li | 606/148 |
| 5,250,055 | 10/1993 | Moore et al. | 606/148 |
| 5,281,234 | 1/1994 | Wilk et al. | 606/139 |
| 5,330,488 | 7/1994 | Goldrath | 606/148 |
| 5,364,410 | 11/1994 | Failla et al. | 606/148 |
| 5,387,227 | 2/1995 | Grice | 606/222 |
| 5,403,329 | 4/1995 | Hinchcliffe | 606/147 |
| 5,462,560 | 10/1995 | Stevens | 606/144 |
| 5,462,561 | 10/1995 | Voda | 606/139 |
| 5,486,183 | 1/1996 | Middleman et al. | 606/127 |
| 5,503,634 | 4/1996 | Christy | 606/144 |
| 5,573,542 | 11/1996 | Stevens | 606/133 |

FOREIGN PATENT DOCUMENTS

| | | | |
|---|---|---|---|
| 4-226643 | 8/1992 | Japan | 606/222 |
| 404226643 | 8/1992 | Japan | 606/222 |
| 969240 | 10/1982 | U.S.S.R. | A61B 17/04 |
| 0242110 | 11/1925 | United Kingdom | 112/80.03 |
| 242110 | 11/1925 | United Kingdom | 112/80.03 |
| 0639845 | 7/1950 | United Kingdom | 112/80.03 |
| 639845 | 7/1950 | United Kingdom | 112/80.03 |

OTHER PUBLICATIONS

English translation of Create Medic brochure, titled "CLINY Percutaneous Gastropexy for Percutaneous Endoscopic Gastrostomy", 5 pages, undate.

Create Medic brochure, titled "CLINY Percutaneous Gastropexy for Percutaneous Endoscopic Gastromony", 4 pages, undated.

R–Med. Inc. brochure, "Riza – Ribe Needle" undated, 5 pages.

Brochure—Ideas for Medicine Inc., Grice Suture Needle.

*Primary Examiner*—Gary Jackson

[57] ABSTRACT

A double needle ligature device for efficiently creating a loop suture for closing wounds, such as trocar wounds. The device preferably includes a double needle assembly to ensure that the suture is positively held in place during needle retraction.

12 Claims, 7 Drawing Sheets

DOUBLE NEEDLE LIGATURE DEVICE

CROSS-REFERENCE TO RELATED APPLICATIONS

This is a continuation of application Ser. No. 08/255,363 filed on Jun. 8, 1994 now abandoned, which is a continuation-in-part of U.S. patent application Ser. No. 08/134,263 filed Oct. 8, 1993, now U.S. Pat. No. 5,462,560.

FIELD OF THE INVENTION

This invention relates to medical devices used to close surgical wounds, and in particular to a fixed double-needle ligature device particularly useful for creating circumferential ligatures as are needed in, for example, endoscopic surgery.

BACKGROUND OF THE INVENTION

During endoscopic surgery, the surgeon often creates a trocar wound; a round hole in tissue that exposes the inside of a body cavity, such as the abdomen during laparoscopy. Once the surgery is completed, the trocar wound must be closed. The difficulty lies in creating a loop suture to complete circumferential ligatures around such wounds. More precisely, it is difficult to loop a suture into a body cavity on one side of a wound and get the suture to exit the body cavity on the other side of the wound so the suture ends can be tied to close the trocar wound.

A prior art solution involves using a single needle device, such as the Grice Suture Needle, marketed by Ideas for Medicine, Inc. In this prior art device, the needle is first forced through the tissue while carrying the end of a suture into the body cavity. The needle is then retracted (leaving the end of the suture in the body) and is inserted again on the other side of the wound. A grasper is used to guide the end of the suture to the tip of the reinserted needle. The needle includes a suture holding indentation near its tip in which the suture is secured as the needle is again withdrawn. The suture is then tied to close the wound.

While the prior art procedure is adequate for wound closure, the single needle procedure includes sequential insertions of the needle into the body cavity, requiring significant surgical skill and manipulation. The sequential process also takes significant time to complete. Further, loss of the suture end from the needle as it is withdrawn is a problem.

It would therefore be advantageous to have a device which could create a loop around a wound, such as a trocar wound, in a shorter time or with less surgical manipulation, in a manner which minimizes the chance of inadvertently losing hold of the suture during needle withdrawal.

SUMMARY OF THE INVENTION

In order to address these concerns, the present invention is directed to a device which includes two needles mounted substantially parallel and separated by a distance greater than the diameter of the wound to be closed.

In a first form of the invention, the ligature device comprises two main parts: a needle assembly and a rod assembly. In this embodiment, the needle assembly is made up of a needle support means (usually a plastic, generally rectangularly shaped bar) for holding needles; first and second hollow needles, each of the needles having a shaft, a proximal end, a distal end, and a sharpened distal tip, and the needles are mounted on the needle support means at their proximal ends. The needles extend substantially parallel to one another from the support means.

The needle assembly also includes a first suture support means for slidably supporting a suture, the support means comprising a transverse passage, e.g. a hole, across the shaft of the first needle.

The rod assembly of this embodiment includes rod support means for holding rods (again such as a rectangular plastic bar), first and second rods, each of the rods having a shaft, a proximal end, and a distal end, the rods being mounted on the rod support means at their proximal ends. Like the needles, the rods extend substantially parallel to one another from the rod support means. At the distal end of the second rod is positioned a second suture support means for slidably supporting a suture. Preferably this support means is a polymeric or wire filament in the form of a loop.

An important feature of the invention is that the rod assembly is slidably engaged with the needle assembly such that the first and second rods are positioned within the first and second needles and the rod assembly is movable with respect to the needle assembly from a rod extended position to a rod retracted position. When the rod assembly is in the rod extended position, the distal end of the first rod extends past the transverse passage in the first needle. At the same time, this configuration allows the second suture support means (i.e. the loop) to extend past the distal end of the second needle.

In another embodiment, the invention is a ligature device which includes (1) a needle assembly comprising first and second hollow needles mounted on a first handle, each of the needles having a shaft, a proximal end, a distal end, the needles being mounted on the first handle at their proximal ends and extending substantially parallel to one another from the first handle; and (2) a rod assembly comprising a rod mounted on a second handle, the rod having a shaft, a proximal end, and a distal end, the rod being mounted on the second handle at its proximal end and extending substantially perpendicular to the handle, a loop filament extending from the distal end of the rod; wherein the rod assembly is slidably engagable with the needle assembly such that the rod can be positioned within the second needle and the rod assembly is movable with respect to the needle assembly from a rod extended position to a rod retracted position, and, when the rod assembly is in the rod extended position, the loop extends past the distal end of the second needle.

In a preferred form of this embodiment the loop is formed of a shape memory alloy, and the loop, when in the rod extended position, deflects to a position under the distal end of the first needle.

By using the structures disclosed herein, the suture loop necessary for closing a trocar type wound can be quickly created by ensuring that the suture is carefully and firmly held within the needles of the device.

BRIEF DESCRIPTION OF THE DRAWINGS

The invention will be better understood by reference to the appended drawings of which.

DETAILED DESCRIPTION OF THE INVENTION

The apparatus of the invention and the method by which it is used is shown in detail in FIGS. 1 through 8.

Figure 1:
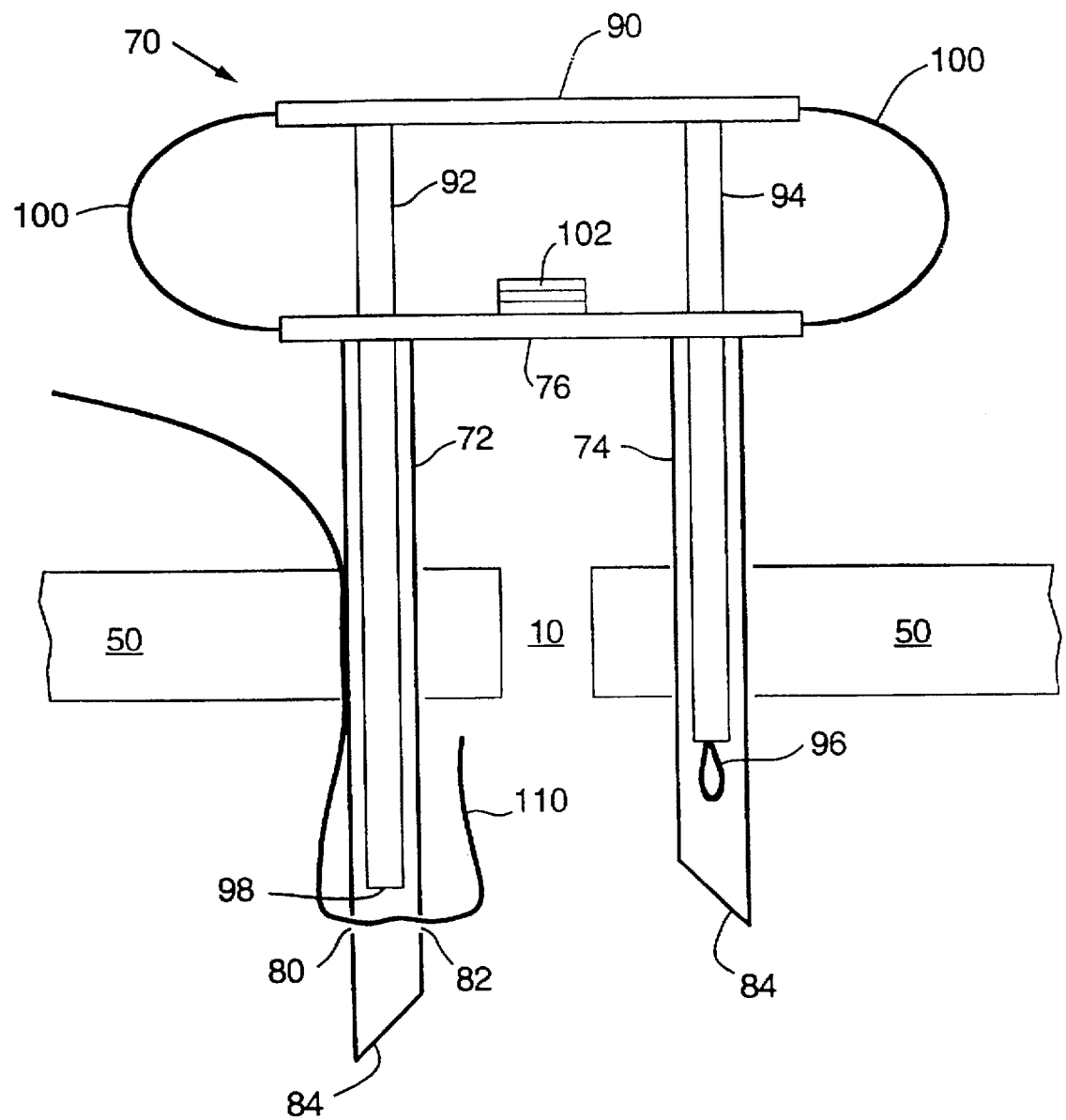
FIG. 1 is a side view of a first embodiment of the invention in its relaxed or rod retracted position while inserted into a body cavity.
Figure 2:
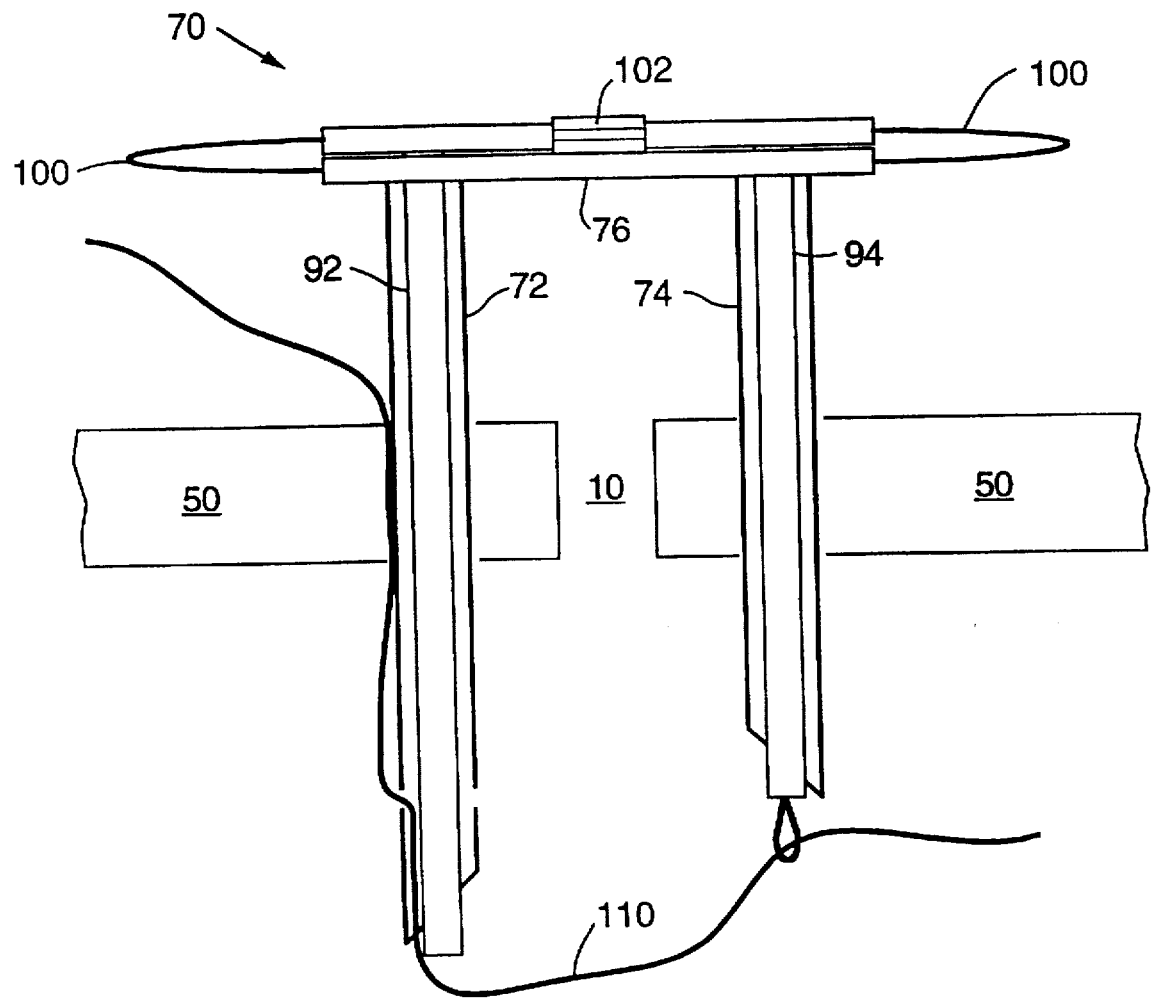
FIG. 2 is a side view of the device of FIG. 1 in a compressed or rod extended position.

A first embodiment of the invention is shown in FIG. 1, designated in its entirety by reference number 70. Device 70 includes two hollow needles, suture feed needle 72 and suture retractor needle 74. A needle separation bar (and handle) 76 holds needles 72 and 74 a distance apart and substantially parallel to each other. Feed needle 72 includes aligned holes 80 and 82 near its tip 84. Needle tips 84 on each of needles 72 and 74 have angled cutting ends for easier insertion through tissue. While FIG. 2 shows needle 74 being shorter than the feed needle 72, this is not necessary. However, to date it appears that the uneven length of the needles facilitates the ability to secure the fascia in a proper technical form.

A rod positioner bar 90 secures suture feed rod 92 to retractor rod 94. Rods 92 and 94 are held parallel to each other and are spaced the same distance apart as the needles 72 and 74. Rod 92 inserts into feed needle 72 and rod 94 inserts into loop needle 74.

A suture engaging loop 96 is attached to the end of rod 94. The loop is formed from a filament of metal or plastic, such as polyethylene. Any material which will form the loop and which is inert with respect to tissue can be used, for example stainless steel.

Preferably the loop is formed from a filament of shape memory alloy (SMA), such as Ni/Ti having the following composition (by weight): 55.7% Ni, 43.9% Ti, 0.20% Cr, 0.033% C, 0.069% O, 0.0019% H, and 0.0961% other elements, which alloy available from Shape Memory Applications, Inc. of Sunnyvale, Calif. under the name NiTi Superelastic Wire Loops Cr-Dp, as drawn, oxide ($A_f$=−1.5 degrees C.). An object having a "pre-formed" shape (and made from SMA in its superelastic form) can be contorted out its pre-formed shape when a contorting force is applied to it, but the object will return to its original "pre-formed" shape when the contorting force is removed. Thus, for example, it may be preferable to form the loop of a filament of superelastic SMA when the ligature device is used in an endoscopic procedure, where it is required that the loop be inserted into a small loop needle 74.

By "superelastic" SMA, it is meant that the Ni/Ti alloy is in a form which does not require the application of heat or stress to cause the loop, in this case, to take the "memorized" shape. SMA's are described in U.S. Pat. No. 5,067,957, which is incorporated herein by reference. However, the superelastic form (as opposed to forms which require heat or stress activation) has been found to be most useful in the present invention.

In order to minimize the degree of manipulation of the device by the surgeon, the degree of insertion of rods 92 and 94 into the needles 72 and 74 can advantageously be controlled by a biasing mechanism 100. Biasing mechanism 100 connects needle handle or bar 76 to bar 90 to provide a flexing motion. In a form of the first embodiment, biasing mechanism 100 is formed from plastic or metal tensioners to create a spring tension when forced out of its relaxed state. In its relaxed state, as shown in FIG. 1, biasing mechanism 100 holds bars 76 and 90 apart by such a distance that the end of rod 92 will not pass holes 80 and 82 in needle 72, and loop 96 does not extend from the end of needle 74.

Biasing mechanism 100 is closed by squeezing bars 76 and 90 together, as shown in FIG. 2. When bars 76 and 90 meet, feed rod 92 is forced beyond holes 80 and 82 and loop 96 extends beyond the tip of loop needle 74. Biasing mechanism 100 flexes as bars 76 and 90 are squeezed together. Biasing mechanism 100 supplies a spring pressure when compressed such that when the bars 76 and 90 are released, the device will return to the relaxed state shown in FIG. 1.

Figure 6:
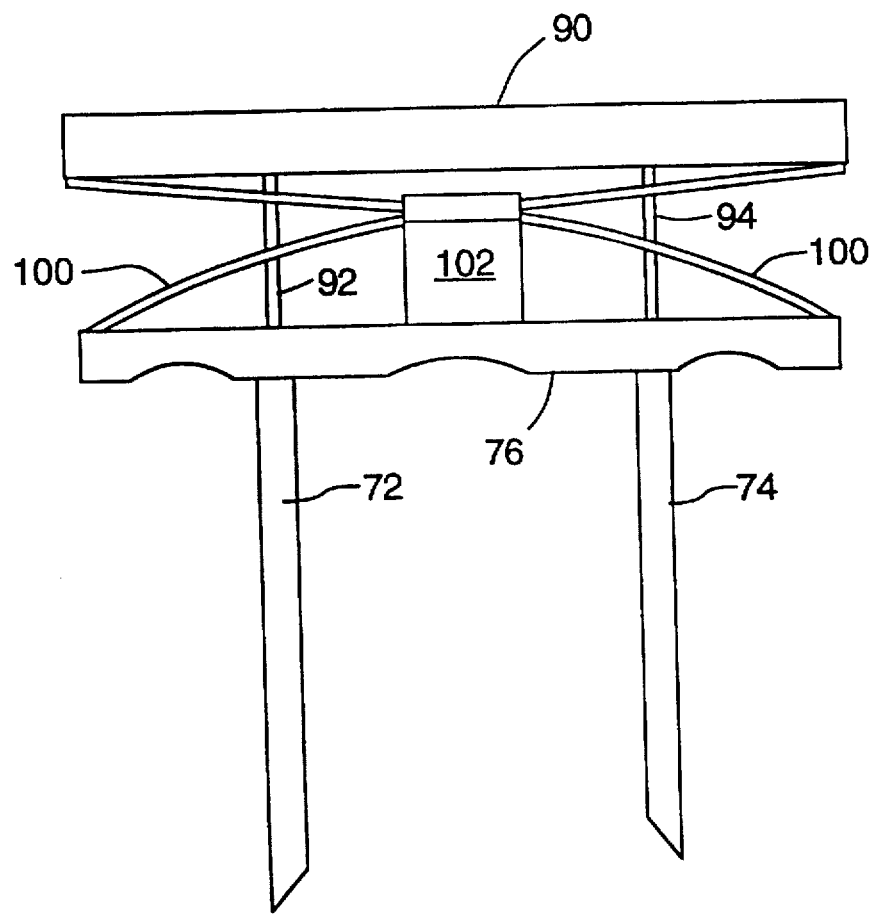
FIG. 6 show an alternate embodiment of the invention showing a different, leaf spring-type biasing mechanism.

Other types of biasing mechanisms well known to those in the art may be substituted for the mechanism 100. For example, a simple leaf spring mechanism mounted between bars 76 and 90 could be used, as shown in FIG. 6.

Typical dimensions for the elements of the device are as follows, using the embodiment shown in FIG. 6 as an example. The distance between the bars 76 and 90 when forced fully apart, about 1.5 inches. The needles 72 and 74 (formed from stainless steel hypodermic tubing 0.088 o.d. and 0.058 i.d.) are centered laterally on bar 76, approximately 0.8 inches apart. Bars 76 and 90 are approximately 3 inches wide. Rod 92 is a 0.045 inch diameter solid stainless steel rod which measures about 5.6 inches in total length, measured from the top of bar 76, thus extending through needle 72 when fully extended, since needle 72 is approximately 4.75 inches long. Needle 74 is approximately 4 inches long. Rod 94 is about 0.056 inches in diameter and about 3.75 inches in length, extending a total of 5.6 inches when combined with loop 96. As springs 100, stainless steel strips about 0.2 inches wide and 0.025 inches thick can be used.

Figure 8:
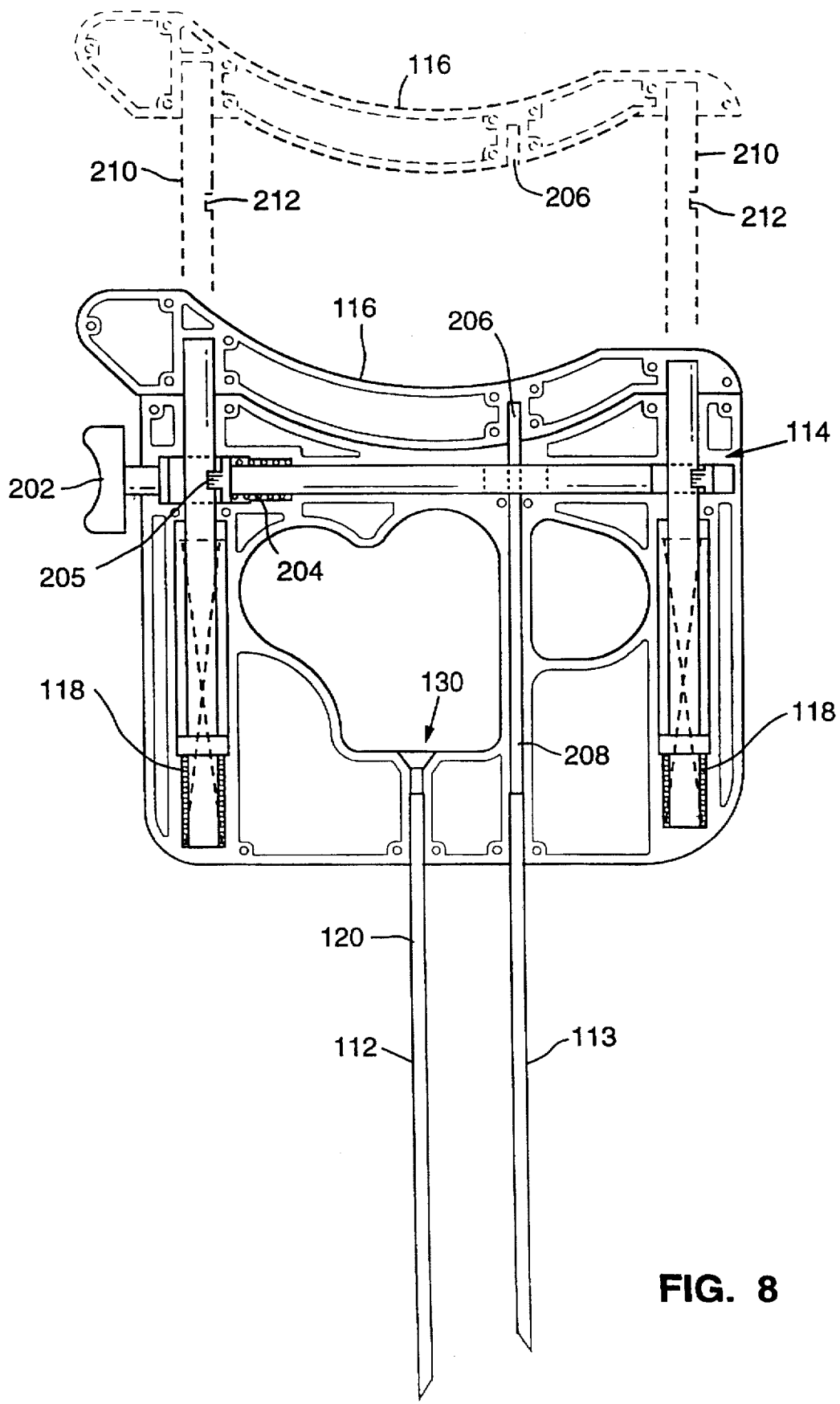
FIG. 8 is a side cross-sectional view of another form of the embodiment shown in FIGS. 7(a) through 7(c), showing a different locking mechanism.

Latching mechanism 102 mounted or formed integrally with bar 76 allows bars 76 and 90 to be securely attached together, as shown in FIG. 2. Latch 102 allows the surgeon to lock biasing mechanism 100 in its compressed position. The surgeon may want to let go of the device while it is inserted into the body cavity without the spring pressure of biasing mechanism 100 returning it to a relaxed position. Alternatively, the mechanism can be design to lock the device in both the extended or retracted positions, as shown in FIG. 8.

Figure 3:
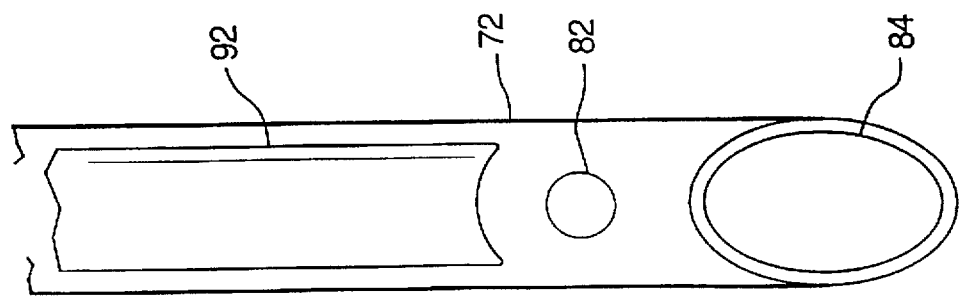
FIG. 3 is a detailed side view showing the feed needle and feed rod.

The end of feed rod 92 is notched, as shown in FIG. 3. Notch 98 is in the same direction as the in-line holes 80 and 82 so as to prevent the suture passing through the holes from being cut by feed rod 92 passing holes 80 and 82.

Figure 4B:
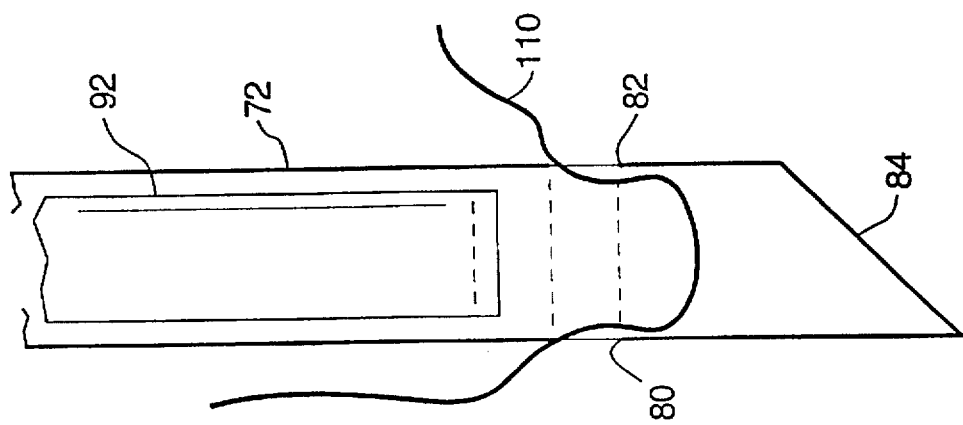
FIGS. 4(a) and 4(b) show the end of the feed needle and feed rod, detailing the primed position of the suture.
Figure 4A:
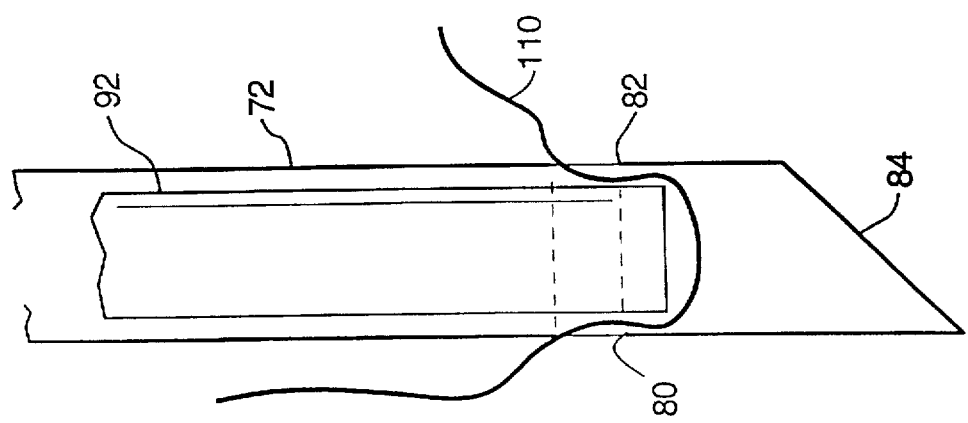
Figure 5:
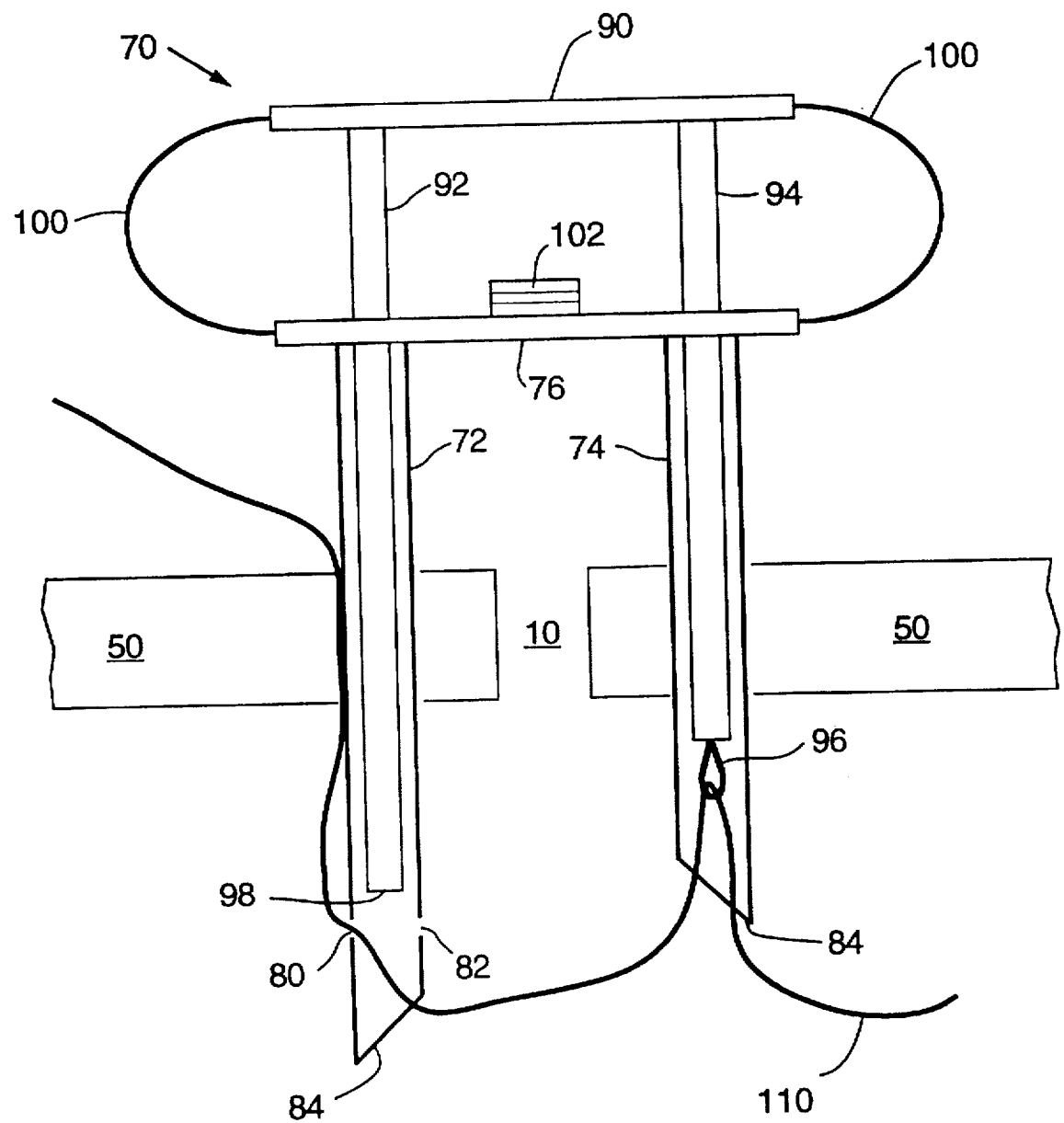
FIG. 5 shows the device of FIG. 1 during retraction of the suture through the outlet needle.

To close a wound, the strategy shown in FIGS. 4(a), 4(b) and 5 is employed. As shown in FIG. 4(a), a suture end 110 is first threaded through holes 80 and 82. The suture is then "primed" by squeezing bars 76 and 90 together until rod 92 forces the suture slightly past holes 80 and 82. Bars 76 and 90 are then released whereby the suture is left in this "primed" position as shown in FIG. 4(b). In its "primed" position, the suture is securely held such that upon insertion of device 70 into the body cavity, the suture will not slip back through holes 80 and 82.

Device 70 is then inserted through a cavity wall so that the ends of needles 72 and 74 penetrate the wall of the cavity, one on each side of the wound 10, as shown in FIG. 1.

In a preferred method of use, the amount of cavity wall used to close the trocar wound can be advantageously increased by inserting the longer feed needle 72 into the tissue first at approximately a 15° angle. The device is then rotated slightly to a position such that needles 72 and 74 are inserted perpendicular to the skin surface adjacent the wound.

Upon insertion of device 70, suture end 110 will be free inside the body cavity. The surgeon then compresses bar 90 and bar 76 such that loop 96 extends beyond the tip of needle 74, as shown in FIG. 2. Rod 92 passes holes 80 and 82 so as to hold a portion of the suture within feed needle 72 secure. A suture grasper (not shown) is then used to grasp suture end 110 and feed it through loop 96. Bars 90 and 76 are subsequently decompressed to withdraw loop 96 inside loop needle 74, as shown in FIG. 5. Suture end 110 is securely held in place by loop 96. Needles 72 and 74 are then removed from the body, thereby withdrawing the suture held by the loop 96.

As device 70 is removed from the body and the tension increases, the portion of the suture in needle 72 will be pulled taut before the tension is great enough to dislodge the end of the suture from loop 96. Thereafter, the suture will slide freely through holes 80 and 82 to supply a sufficient length of suture to permit removal of the suture from the body.

After the device is removed from the body the surgeon can remove the suture from loop 96, allowing suture ends 96 to be tied together.

Figure 7A:
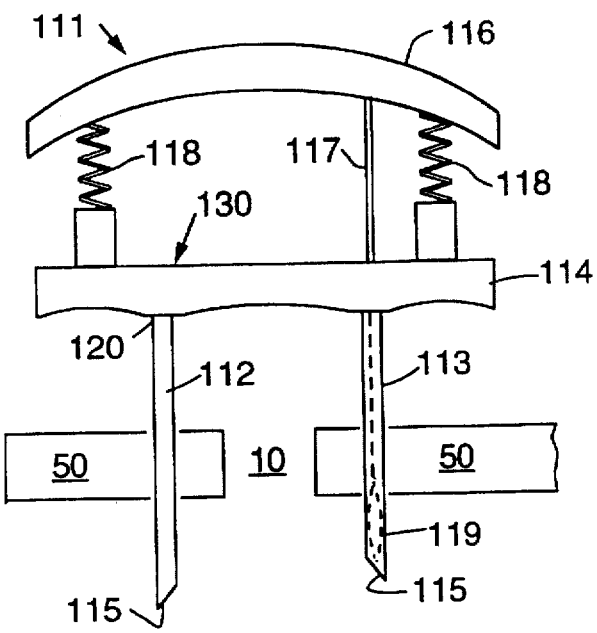
FIG. 7(a) is a side view of an alternate embodiment of the invention in its relaxed or rod retracted position while inserted into a body cavity.
Figure 7B:
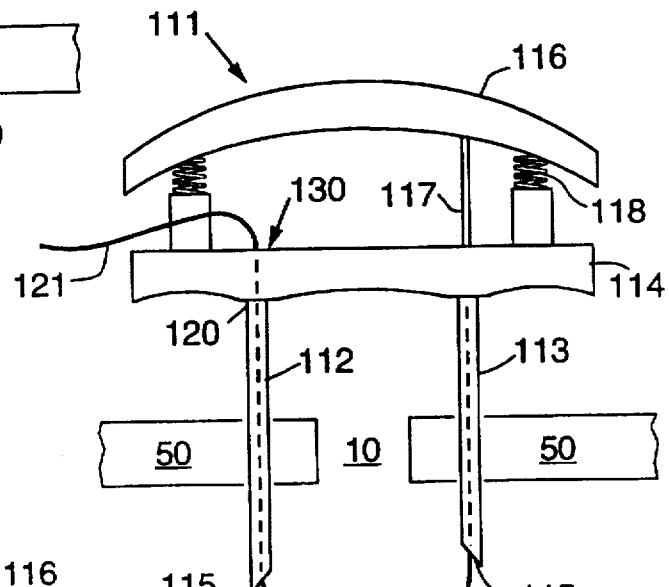
FIG. 7(b) is a side view of the device of FIG. 7(a) in a compressed or rod extended position.
Figure 7C:
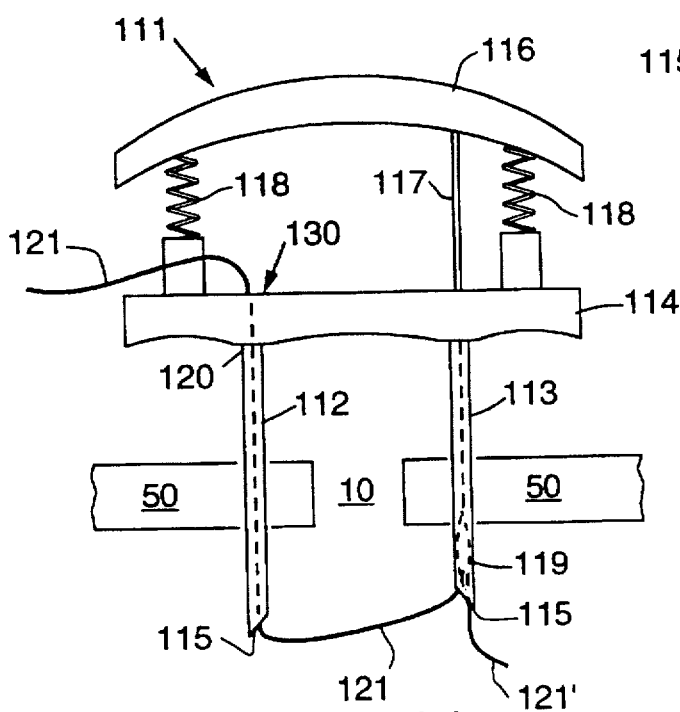
FIG. 7(c) is a side view of the device of FIGS. 7(a) and 7(b) during retraction of a suture.

An alternate embodiment of the invention is shown in FIGS. 7(a)–7(c), designated in its entirety by reference number 111. This embodiment provides a slightly simplified arrangement in which, essentially, rod 92 of the first embodiment can be eliminated. Device 111 includes two hollow needles, suture feed needle 112 and suture retractor needle 113. A needle separation bar 114 holds needles 112 and 113 a distance apart and substantially parallel to each other. Needle separation bar 114 has in it an opening 130, leading to an opening in needle 112 at its proximal end 120. Proximal end 120 is positioned in needle separation bar opening 130. Needle tips 115 on each of needles 112 and 113 have angled cutting ends for easier insertion through tissue.

While FIGS. 7(a)–7(c) show retractor needle 113 being shorter than feed needle 112, this is not necessary. However, as discussed above, to date it appears that the uneven length of the needles facilitates the ability to secure the fascia in a proper technical form.

A suture engaging articulating loop 119 is attached to the end of rod 117. The loop is formed from a filament of metal or plastic such as polyethylene. Any material which will form the loop and which is inert with respect to tissue can be used. As discussed above, in this embodiment, however, it is preferable to form the loop of a filament of superelastic SMA.

Retractor rod 117 is secured to handle 116. Rod 117 inserts into retractor needle 113. Biasing mechanism 118 connects handle 116 to needle separation bar 114 to provide flexing motion.

In a relaxed state, as shown in FIG. 7(a), biasing mechanism 118 holds handle 116 and needle separation bar 114 apart by such a distance that loop 119 does not extend from the end of needle 113.

Biasing mechanism 118 is closed by squeezing handle 116 and bar 114 together, as shown in FIG. 7(b). When handle 116 is squeezed downwardly toward bar 114, loop 119 extends beyond the tip of loop needle 113 and past the distal end of needle 112. The coil springs of biasing mechanism 118 compress as handle 116 and bar 114 are squeezed together. Biasing mechanism 118 supplies a spring pressure such that when the handle 116 and bar 114 are released, the device will return to the relaxed state shown in FIG. 7(c).

As discussed above other types of biasing mechanisms are well known to those in the art and these other biasing mechanisms (leaf springs, other material such as flexible polymeric materials, etc.) may be substituted for the coil springs shown.

A latching mechanism (not shown in FIG. 7, see 102 in FIG. 2 or FIG. 8) can be mounted or formed integrally with bar 114 to allow bar 114 and handle 118 to be securely, but temporarily, attached together. Such a latch allows the surgeon to lock biasing mechanism 118 in its compressed position. The surgeon may want to release the device while it is inserted into the body cavity without the spring force the biasing mechanism 118 returning it to a relaxed position.

To close a wound, the strategy shown in FIGS. 7(a)–7(c) is employed. As shown in FIG. 7(a), device 111 is inserted through a cavity wall so that the ends of needles 112 and 113 penetrate the wall of the cavity 50 one needle on each side of the wound.

In a preferred method of use, the amount of cavity wall used to close the trocar wound can be advantageously increased by inserting the longer feed needle 112 into the tissue first at approximately a 15° angle. The device is then rotated slightly to a position such that needles 112 and 113 are inserted perpendicular to the skin surface adjacent to the wound.

Upon insertion of device 111, the surgeon compresses handle 116 and bar 114 causing articulating loop 119 to extend beyond the tip of needle 112 and deflect (using the superelastic SMA) completely under the distal end of needle 112 as shown in FIG. 7(b). Then, an end 121' of a suture 121 is fed through opening 130 in needle separation bar 114 and then through opening 120 in needle 112 and through loop 119 inside the body cavity. Handle 116 and bar 114 are decompressed to withdraw loop 119 inside loop needle 113 as shown in FIG. 7(c). Suture end 121' is firmly held in place by loop 119. Needles 112 and 113 are then removed from the body, thereby withdrawing suture 121 held by loop 119.

As device 111 is removed from the body and the tension increases, the portion of the suture in needle 112 will be pulled taut before the tension is great enough to dislodge the end of the suture from loop 119. Thereafter, the suture will slide freely through needle 112 to supply a sufficient length of suture to permit completion of removal of device 111 from the body.

After device 111 is removed from the body the surgeon can remove suture end 121' from loop 119, allowing suture 121 to be tied.

Referring now to FIG. 8, another view having the same basic structure as the device shown in FIGS. 7(a) through 7(c) is shown, though the device of FIG. 8 provides an altered configuration which is easier for the physician to hold in use. The elements of FIG. 8 are numbered consistently with those used in FIGS. 7. Not shown in FIG. 8 is rod 117 of FIGS. 7, which rod would be positioned in opening 206 and pass through passage 208 of FIG. 8. As can be seen bar 114 of the previous embodiment has been reconfigured in the embodiment of FIG. 8, indicating that any number of configurations might be adopted which nevertheless incorporate the key elements of the invention. In this embodiment, the reconfiguration permits opening 130 to be positioned as shown.

FIG. 8 also shows a different locking mechanism for the device, which, like the lock mechanism of FIG. 6 is labelled 202. In this embodiment, however, the lock utilizes a horizontally disposed cross bar, biased using spring 204 and latch 205. Latch 205 is forced into depressions 212 formed in support columns 210 for handle 116. Thus, the device can be locked in either the extended or the retracted position. The lock is released by pressing button 202.

It should be noted that FIG. 8 includes the handle 116 shown both in the retracted and the extended positions.

While the invention has been described with reference to the closure of trocar wounds arising from endoscopic surgery, those skilled in the art will recognize that the invention will be useful for any procedure requiring ligature of a major vessel or organ. Such procedures would include, for example, a bladder suspension, a uterine neck ligation for a laparoscopic assisted vaginal hysterectomy (LAVH), an appendectomy or a laparoscopic bowel resection.

Although only the most preferred embodiments of the invention has been shown and described, many modifications and rearrangements of the components of the invention, which nevertheless include the key features thereof, will be apparent to those skilled in the art of needle ligature devices particularly useful for creating circumferential ligatures. Thus, such modifications are considered to be within the scope of the appended claims.

What is claimed is:

1. A ligature device including:
   (1) a needle assembly comprising
      (a) needle support means for holding needles;
      (b) first and second hollow needles, each of said needles having a shaft, a proximal end having a proximal end opening, a distal end having a distal end opening, and a sharpened distal tip, said needles being mounted on said needle support means at their proximal ends and extending substantially parallel to one another from said support means; and
   (2) a rod assembly consisting of
      a rod and a filament loop of shape memory alloy (SMA), said rod having a shaft, a proximal end, and a distal end, and being mounted on a rod handle at said proximal end, and said loop being positioned at said distal end of said rod;
      said rod assembly connected to but slidably engaged with said needle assembly such that said rod is positioned within said first needle and said rod assembly is movable with respect to said needle assembly from a rod extended position to a rod retracted position, and, when said rod assembly is in said rod extended position, said filament loop extends past said distal end of said first needle such that said loop is deflected by said SMA to a position completely under said distal end opening of said second needle.

2. A ligature device comprising
   (1) a needle assembly comprising
      (a) needle support means for holding needles;
      (b) first and second hollow needles, each of said needles having a shaft, a proximal end having a proximal end opening, a distal end having a distal end opening, and a sharpened distal tip, said needles being mounted on said needle support means at their proximal ends and extending substantially parallel to one another from said support means; and
   (2) a rod assembly consisting of a rod and a filament loop of shape memory alloy (SMA), said rod having a shaft, a proximal end, and a distal end, and being mounted on a rod handle at said proximal end, and said loop being positioned at said distal end of said rod; said rod assembly connected to but slidably engaged with said needle assembly such that said rod is positioned within said first needle and said rod assembly is movable with respect to said needle assembly from a rod extended position to a rod retracted position, and, when said rod assembly is in said rod extended position, said filament loop extends past said distal end of said first needle such that said loop is deflected by said SMA to a position completely under said distal end opening of said second needle; and biasing means positioned between said needle support means and said rod support means for urging said needle and rod assemblies toward said rod retracted position.

3. A ligature device according to claim 2 wherein said biasing means comprises a pair of tensioned metal or plastic strips.

4. A ligature device comprising
   (1) a needle assembly comprising
      (a) needle support means for holding needles;
      (b) first and second hollow needles, each of said needles having a shaft, a proximal end having a proximal end opening, a distal end having a distal end opening, and a sharpened distal tip, said needles being mounted on said needle support means at their proximal ends and extending substantially parallel to one another from said support means;
   (2) a rod assembly consisting of a rod and a filament loop of shape memory alloy (SMA), said rod having a shaft, a proximal end, and a distal end, and being mounted on a rod handle at said proximal end, and said loop being positioned at said distal end of said rod; said rod assembly connected to but slidably engaged with said needle assembly such that said rod is positioned within said first needle and said rod assembly is movable with respect to said needle assembly from a rod extended position to a rod retracted position, and, when said rod assembly is in said rod extended position, said filament loop extends past said distal end of said first needle such that said loop is deflected by said SMA to a position completely under said distal end opening of said second needle; and a releasable lock for locking said needle and rod assemblies together in said rod extended position.

5. A ligature device comprising
   (1) a needle assembly comprising
      (a) needle support means for holding needles;
      (b) first and second hollow needles, each of said needles having a shaft, a proximal end having a proximal end opening, a distal end having a distal end opening, and a sharpened distal tip, said needles being mounted on said needle support means at their proximal ends and extending substantially parallel to one another from said support means; and
   (2) a rod assembly consisting of a rod and a filament loop of shape memory alloy (SMA), said rod having a shaft, a proximal end, and a distal end, and being mounted on a rod handle at said proximal end, and said loop being positioned at said distal end of said rod; said rod assembly connected to but slidably engaged with said needle assembly such that said rod is positioned within said first needle and said rod assembly is movable with respect to said needle assembly from a rod extended position to a rod retracted position, and, when said rod assembly is in said rod extended position, said filament loop extends past said distal end of said first needle such that said loop is deflected by said SMA to a position completely under said distal end opening of said second needle; and wherein said second hollow needle is longer than said first hollow needle.

6. A ligature device including:

(1) a needle assembly comprising first and second hollow needles mounted on a first handle, each of said needles having a shaft, a proximal end, a distal end, said needles being mounted on said first handle at their proximal ends and extending substantially parallel to one another from said first handle, and each of said needles having openings at their proximal and distal ends and no other openings; and (2) a rod assembly consisting of a second handle having a single rod mounted thereon, said rod having a shaft, a proximal end, and a distal end, said rod being mounted on said second handle at its proximal end and extending substantially perpendicular to said handle, a loop filament extending from said distal end of said rod;

said rod assembly being connected to and slidably engaged with said needle assembly such that said rod can be positioned within said second needle and said rod assembly is movable with respect to said needle assembly from a rod extended position to a rod retracted position, and, when said rod assembly is in said rod extended position, said loop extends past said distal end of said second needle and is deflected to a position adjacent the distal end of said first needle such that a suture which is passed through said first needle and out said distal end thereof will pass through said loop, and when said rod assembly is in said rod retracted position, said loop and said suture are positioned within said second needle, securing the suture to the second needle.

7. A ligature device according to claim 6 wherein said loop is formed of a shape memory alloy.

8. A ligature device including:

(1) a needle assembly comprising first and second hollow needles mounted on a first handle, each of said needles having a shaft, a proximal end, a distal end, said needles being mounted on said first handle at their proximal ends and extending substantially parallel to one another from said first handle, and each of said needles having openings at their proximal and distal ends and no other openings;

(2) a rod assembly consisting of a second handle having a single rod mounted thereon, said rod having a shaft, a proximal end, and a distal end, said rod being mounted on said second handle at its proximal end and extending substantially perpendicular to said handle, a loop filament extending from said distal end of said rod;

said rod assembly being connected to and slidably engaged with said needle assembly such that said rod can be positioned within said second needle and said rod assembly is movable with respect to said needle assembly from a rod extended position to a rod retracted position, and, when said rod assembly is in said rod extended position, said loop extends past said distal end of said second needle and is deflected to a position adjacent the distal end of said first needle such that a suture which is passed through said first needle and out said distal end thereof will pass through said loop; and biasing means for urging said needle and rod assemblies toward said rod retracted position.

9. A ligature device according to claim 8 wherein said biasing means comprises a pair of tensioned metal or plastic strips.

10. A ligature device including;

(1) a needle assembly comprising first and second hollow needles mounted on a first handle, each of said needles having a shaft, a proximal end, a distal end, said needles being mounted on said first handle at their proximal ends and extending substantially parallel to one another from said first handle, and each of said needles having openings at their proximal and distal ends and no other openings;

(2) a rod assembly consisting of a second handle having a single rod mounted thereon, said rod having a shaft, a proximal end, and a distal end, said rod being mounted on said second handle at its proximal end and extending substantially perpendicular to said handle, a loop filament extending from said distal end of said rod;

said rod assembly being connected to and slidably engaged with said needle assembly such that said rod can be positioned within said second needle and said rod assembly is movable with respect to said needle assembly from a rod extended position to a rod retracted position, and, when said rod assembly is in said rod extended position, said loop extends past said distal end of said second needle and is deflected to a position adjacent the distal end of said first needle such that a suture which is passed through said first needle and out said distal end thereof will pass through said loop: and a releasable lock for locking said needle and rod assemblies in said rod extended position.

11. A ligature device including:

(1) a needle assembly comprising first and second hollow needles mounted on a first handle, each of said needles having a shaft, a proximal end, a distal end, said needles being mounted on said first handle at their proximal ends and extending substantially parallel to one another from said first handle, and each of said needles having openings at their proximal and distal ends and no other openings;

(2) a rod assembly consisting of a second handle having a single rod mounted thereon, said rod having a shaft, a proximal end, and a distal end, said rod being mounted on said second handle at its proximal end and extending substantially perpendicular to said handle, a loop filament extending from said distal end of said rod;

said rod assembly being connected to and slidably engaged with said needle assembly such that said rod can be positioned within said second needle and said rod assembly is movable with respect to said needle assembly from a rod extended position to a rod retracted position, and, when said rod assembly is in said rod extended position, said loop extends past said distal end of said second needle and is deflected to a position adjacent the distal end of said first needle such that a suture which is passed through said first needle and out said distal end thereof will pass through said loop; and wherein said first needle is longer than said second needle.

12. A ligature device including:

(1) a needle assembly comprising first and second hollow needles mounted on a first handle, each of said needles having a shaft, a proximal end, a distal end, said needles being mounted on said first handle at their proximal ends and extending substantially parallel to one another from said first handle, said first handle having an opening, said first needle having an opening in said proximal end, said proximal end of said first needle being positioned in said opening of said first handle; and (2) a rod assembly consisting of a rod mounted on a second handle, said rod having a shaft, a proximal end, and a distal end, said rod being mounted on said second handle at its proximal end and extending from said second handle, (3) means for capturing a suture extending from said distal end of said rod;

said rod assembly being connected to and slidably engaged with said needle assembly such that said rod is positioned within said second needle and said rod assembly is movable with respect to said needle assembly from a rod extended position to a rod retracted position, and when said rod assembly is in said rod extended position said means for capturing a suture extends past said distal end of said second needle; said device further comprising biasing means for urging said needle and rod assemblies toward said rod retracted position and a releasable lock for locking said needle and rod assemblies in said rod extended position; and wherein said means for capturing said suture consists of a filament loop of shape memory alloy, which, when in the rod extended position, deflects to a position under said distal end of said first needle.

* * * * *